United States Patent

Petersen et al.

[11] Patent Number: 4,820,716
[45] Date of Patent: Apr. 11, 1989

[54] 7-(1-PYRROLIDINYL)-QUINOLONECARBOXYLIC ACID DERIVATIVES

[75] Inventors: Uwe Petersen, Leverkusen; Klaus Grohe, Odenthal; Hans-Joachim Zeiler, Velbert; Karl G. Metzger, Wuppertal-Elberfeld, all of Fed. Rep. of Germany

[73] Assignee: Bayer Aktiengesellschaft, Leverkusen, Fed. Rep. of Germany

[21] Appl. No.: 13,744

[22] Filed: Feb. 12, 1987

[30] Foreign Application Priority Data

Mar. 1, 1986 [DE] Fed. Rep. of Germany ....... 3606698

[51] Int. Cl.$^4$ ............... A61K 31/47; A61K 31/435; C07D 215/56; C07D 471/04
[52] U.S. Cl. .................... 514/312; 514/300; 514/187; 514/186; 546/123; 546/156; 546/5
[58] Field of Search ............ 514/312, 187; 546/156, 546/6, 5

[56] References Cited

U.S. PATENT DOCUMENTS

| 4,499,091 | 2/1985 | Wentland et al. | 546/156 |
| 4,556,658 | 12/1985 | Grohe et al. | 546/156 |
| 4,563,459 | 1/1986 | Grohe et al. | 546/156 |
| 4,571,396 | 2/1986 | Hutt et al. | 546/156 |
| 4,620,007 | 10/1986 | Grohe et al. | 544/128 |
| 4,623,650 | 10/1986 | Gilligan et al. | 514/236 |
| 4,670,444 | 6/1987 | Grohe et al. | 546/156 |
| 4,727,080 | 2/1988 | Soler | 546/156 |

FOREIGN PATENT DOCUMENTS

| 0047005 | 3/1982 | European Pat. Off. . |
| 131839 | 1/1985 | European Pat. Off. ............ 546/156 |
| 0153828 | 9/1985 | European Pat. Off. . |
| 0153580 | 9/1985 | European Pat. Off. . |
| 0160578 | 11/1985 | European Pat. Off. . |
| 187085 | 7/1986 | European Pat. Off. ............ 514/312 |
| 201829 | 11/1986 | European Pat. Off. . |
| 3420743 | 12/1985 | Fed. Rep. of Germany . |

OTHER PUBLICATIONS

Derwent Abstract for EP131839 (1/23/85).
Derwent Abstract for EP187085 (7/9/86).

Primary Examiner—Donald G. Daus
Assistant Examiner—F. Bernhardt
Attorney, Agent, or Firm—Sprung Horn Kramer & Woods

[57] ABSTRACT 7-(1-Pyrrolidinyl)-3-quinolonecarboxylic acid derivatives of the formula

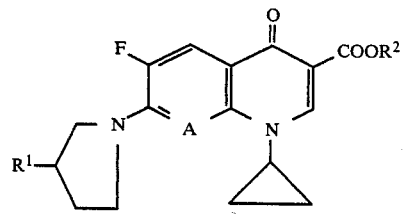

in which
A is CH, CCl, CF or N,
$R^1$ is hydroxyl, hydroxymethyl or mercapto and
$R^2$ is hydrogen, alkyl, having 1 to 4 carbon atoms or (5-methyl-2-oxo-1,3-dioxol-4-yl)methyl,
with the proviso that, when $R^1$ is hydroxy, A is not CF or N, or pharmaceutically acceptable hydrates, or salts thereof, are useful as antibacterials and animal feed utilization promoters.

10 Claims, No Drawings

7-(1-PYRROLIDINYL)-QUINOLONECARBOXYLIC ACID DERIVATIVES

The present invention relates to new 7-(1-pyrrolidinyl)-3-quinolonecarboxylic acid derivatives, to processes for their preparation and to antibacterial agents and fodder additives containing them.

It has already been disclosed that 1-cyclopropyl-6-fluoro-1,4-dihydro-4-oxo-7-(1-piperazinyl)-3-quinolinecarboxylic acid (ciprofloxacin, DE-OS (German Published Specification) No. 3,142,854) and 8-chloro-1-cyclopropyl-6-fluoro-1,4-dihydro-4-oxo-7-(1-piperazinyl)-3-quinolonecarboxylic acids (application Ser. No. 735,500, filed May 17, 1985, now pending) are highly active antibacterial agents.

It has now been found that the new 7-(1-pyrrolidinyl)-3-quinolonecarboxylic acid derivatives of the formula (I)

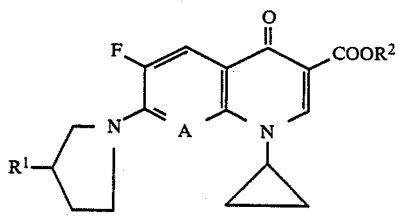

in which
A stands for CH, CCl, CF or N,
$R^1$ stands for hydroxyl, hydroxymethyl or mercapto and
$R^2$ stands for hydrogen, alkyl having 1 to 4 carbon atoms or (5-methyl-2-oxo-1,3-dioxol-4-yl)-methyl,
with the proviso that in the case where $R^1$ stands for hydroxyl A cannot stand for the radical CF or N,
and their pharmaceutically usable hydrates and also the alkali metal, alkaline earth metal, silver and guanidinium salts of the parent carboxylic acids have a high antibacterial action in the Gram-positive and Gram-negative range.

They are therefore suitable for use as active compounds for human and veterinary medicine, veterinary medicine also including the treatment of fish for the therapy or prevention of bacterial infections.

Preference is given to those compounds of the formula (I) in which
A stands for CH, CCl, CF or N,
$R^1$ stands for hydroxyl, hydroxymethyl or mercapto and
$R^2$ stands for hydrogen, methyl, ethyl, propyl or isopropyl,
with the proviso that in the case where $R^1$ stands for hydroxyl, A cannot stand for the radical CF or N,
and their pharmaceutically usable hydrates and also the alkali metal, alkaline earth metal, silver and guanidinium salts of the parent carboxylic acids.

Particular preference is given to those compounds of the formula (I) in which
A stands for CH, CCl or CF,
$R^1$ stands for hydroxyl or hydroxymethyl and
$R^2$ stands for hydrogen, methyl or ethyl,
with the proviso that in the case where $R^1$ stands for hydroxyl A cannot stand for the radical CF,
and their pharmaceutically usable hydrates and also the alkali metal, alkaline earth metal, silver and guanidinium salts of the parent carboxylic acids.

It has further been found that the compounds of the formula (I) are obtained when compounds of the formula (II)

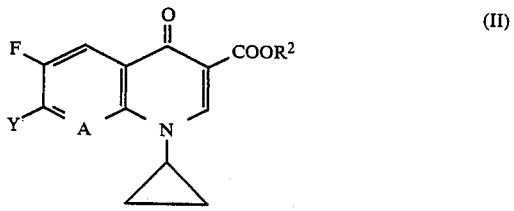

in which
A and $R^2$ have the abovementioned meaning and
Y stands for halogen, in particular fluorine or chlorine, are reacted with pyrrolidines of the formula (III)

in which
$R^1$ has the abovementioned meaning,
if desired in the presence of acid-binding agents (method A).

Compounds according to the invention of the formula (I)

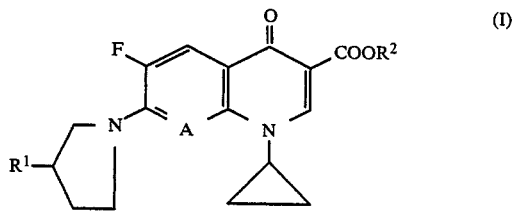

in which
A, $R^1$ and $R^2$ have the abovementioned meaning but $R^2$ cannot be hydrogen, can also be obtained by reacting a compound (IV)

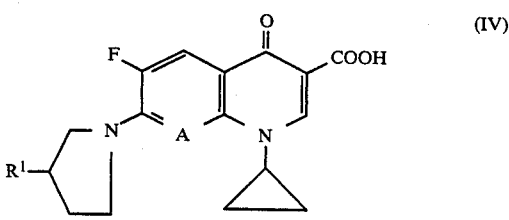

in which
$R^1$ and A have the abovementioned meaning,
with compounds of the formula (V)

in which

R² has the abovementioned meaning but cannot be hydrogen, and

Z stands for hydroxyl or halogen, in particular chlorine, bromine or iodine, if desired in the presence of acid-binding agents or under water-eliminating conditions (method B).

If in the reaction by method A 1-cyclopropyl-6,7-difluoro-1,4-dihydro-4-oxo-3-quinolinecarboxylic acid and 3-hydroxypyrrolidine are used as starting materials, the course of reaction can be represented by the following formula diagram:

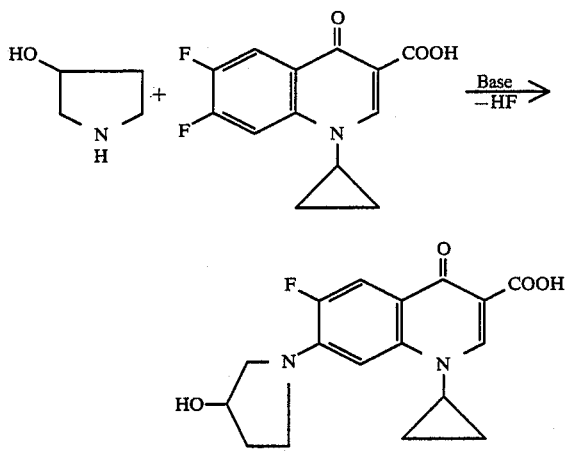

If in the reaction by method B 1-cyclopropyl-6-fluoro-1,4-dihydro-7-(3-hydroxy-1-pyrrolidinyl)-4-oxo-3-quinolinecarboxylic acid and ethyl alcohol are used as starting materials, the course of reaction can be represented by the following formula diagram:

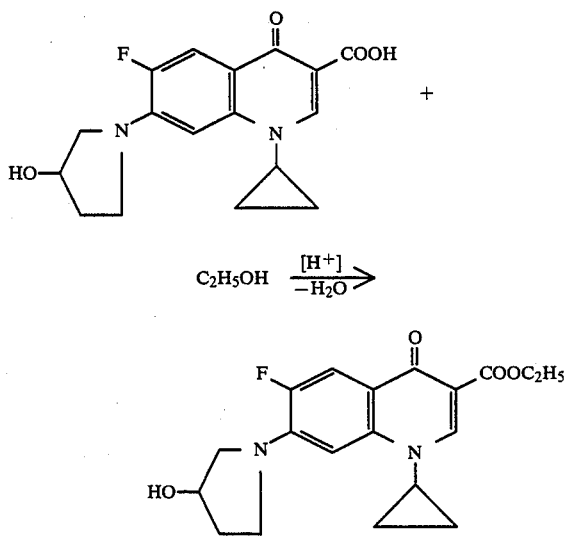

The compounds of the formula (II) used as starting materials are known. Examples which may be mentioned are:

7-chloro-1-cyclopropyl-6-fluoro-1,4-dihydro-4-oxo-3-quinolinecarboxylic acid (U.S. Pat. No. 4,670,444), 1-cyclopropyl-6,7-difluoro-1,4-dihydro-4-oxo-3-quinolinecarboxylic acid (European Patent Application No. 113,091), 8-chloro-1-cyclopropyl-6,7-difluoro-1,4-dihydro-4-oxo-3-quinolinecarboxylic acid (application Ser. No. 735,500, filed May 17, 1985), 1-cyclopropyl-6,7,8-trifluoro-1,4-dihydro-4-oxo-3-quinolinecarboxylic acid (U.S. Pat. No. 4,556,658), 7-chloro-1-cyclopropyl-6-fluoro-1,4-dihydro-4-oxo-1,8-naphthyrine-3-carboxylic acid, ethyl 7-chloro-1-cyclopropyl-6-fluoro-1,4-dihydro-4-oxo-3-quinolinecarboxylate (U.S. Pat. No. 4,670,444), ethyl 1-cyclopropyl-6,7-difluoro-1,4-dihydro-4-oxo-3-quinolinecarboxylate (European Patent Application No. 113,091), ethyl 8-chloro-1-cyclopropyl-6,7-difluoro-1,4-dihydro-4-oxo-3-quinolinecarboxylate (application Ser. No. 735,500, filed May 17, 1985), ethyl 1-cyclopropyl-6,7,8-trifluoro-1,4-dihydro-4-oxo-3-quinolinecarboxylate (U.S. Pat. No. 4,556,658).

The pyrrolidines of the formula (III) used as starting compounds are known. The compounds can be used not only in the form of racemates but also in the form of pure enantiomers which can be obtained by widely practiced methods. The following compounds can be used:

(±)-3-hydroxypyrrolidine,
(+)-3-hydroxypyrrolidine,
(−)-3-hydroxypyrrolidine,
(±)-3-hydroxymethylpyrrolidine,
(+)-3-hydroxymethylpyrrolidine,
(−)-3-hydroxymethylpyrrolidine,
(±)-3-mercaptopyrrolidine,
(+)-3-mercaptopyrrolidine,
(−)-3-mercaptopyrrolidine.

The compounds of the formula (IV) used as starting compounds for method B are new and are prepared by method A of the process according to the invention.

The compounds of the formula (V) used as starting compounds are known. Examples which may be mentioned are methanol, ethanol, propanol, isopropanol, butanol, isobutanol, sec.-butanol, tert.-butanol, methyl iodide, ethyl bromide, propyl chloride, 4-bromomethyl- or 4-chloromethyl-5-methyl-1,3-dioxol-2-one.

The reaction of (II) with (III) using method A, where the pyrrolidines (III) can also be used in the form of their salts, such as, for example, the hydrochlorides, hydrobromides, sulphates or acetates, is preferably carried out in a diluent such as dimethyl sulphoxide, N,N-dimethylformamide, hexamethylphosphoramide, sulpholane, acetonitrile, water, an alcohol such as methanol, ethanol, n-propanol, isopropanol, glycol monomethyl ether or pyridine. It is also possible to use mixtures of these diluents.

The acid-binders used can be any customary inorganic and organic acid-binding agents. These preferably include the alkali metal hydroxides, alkali metal carbonates, organic amines and amidines. Specific examples of particularly suitable acid-binding agents are: triethylamine, 1,4-diazabicyclo[2.2.2]octane (DABCO), 1,8-diazabicyclo[5,4,0]undec-7-ene (DBU) or excess pyrrolidine (III).

The reaction temperatures can be varied within a relatively wide range. In general the process is carried out at between about 20° and 200° C., preferably between 80° and 180° C.

The reaction can be carried out under atmospheric pressure, and also under superatmospheric pressure. In general the process is carried out under pressures between about 1 and 100 bar, preferably between 1 and 10 bar.

In carrying out the process according to the invention, for every mole of carboxylic acid (II) 1 to 15 moles, preferably 1 to 6 moles, of the compound (III) are used.

Free hydroxyl groups can be protected during the reaction by means of a suitable hydroxyl-protecting group, for example by means of the tetrahydropyranyl radical, and be set free again after the reaction has ended.

To prepare the esters according to the invention by method B, the parent carboxylic acid of the formula (IV) is converted at temperatures of about 20° to 200° C., preferably about 60° to 120° C., preferably in excess alcohol in the presence of strong acids, such as sulphuric acid, anhydrous hydrogen chloride, methanesulphonic acid, p-toluenesulphonic acid or acidic ion exchangers. The water of reaction formed can also be removed by azeotropic distillation with chloroform, tetrachloromethane, benzene or toluene.

The alkyl esters can likewise be obtained by reacting an alkali metal salt or amine salt of the parent carboxylic acid of the formula (IV) with an alkyl halide at temperatures of about 0° C. to about 150° C., preferably at 10° C. to 100° C., preferably in a diluent such as dimethyl sulphoxide, dimethylformamide, pyridine, sulpholane or tetramethylurea.

The 5-methyl-2-oxo-1,3-dioxol-4-ylmethyl esters used as prodrug are obtained by reacting an alkali metal salt of the parent carboxylic acid with 4-bromomethyl- or 4-chloromethyl-5-methyl-1,3-dioxol-2-one in a solvent such as dimethylformamide, dimethylacetamide, dimethyl sulphoxide or tetramethylurea at temperatures of about 0° C. to 100° C., preferably 0° C. to 50° C.

The alkali metal or alkaline earth metal salts of the carboxylic acids according to the invention are obtained for example by dissolving the acid in stoichiometrically deficient alkali metal hydroxide or alkaline earth metal hydroxide solution, filtering, and evaporating the filtrate to dryness. The sodium, potassium or calcium salts are pharmaceutically suitable. By reacting an alkali metal salt or alkaline earth metal salt with a suitable silver salt such as silver nitrate, the corresponding silver salts are obtained.

The active compound according to the invention can be present not only as racemates but also as enantiomerically pure compounds.

In addition to the compounds cited in the examples, the following may specifically be mentioned as new active compound:

1-cyclopropyl-6-fluoro-1,4-dihydro-7-[3-(S)-hydroxy-1-pyrrolidinyl]-4-oxo-3-quinolinecarboxylic acid,
1-cyclopropyl-6-fluoro-1,4-dihydro-7-[3-(R)-hydroxy-1-pyrrolidinyl]-4-oxo-3-quinolinecarboxylic acid,
8-chloro-1-cyclopropyl-6-fluoro-1,4-dihydro-7-[3-(S)-hydroxy-1-pyrrolidinyl]-4-oxo-3-quinolinecarboxylic acid,
8-chloro-1-cyclopropyl-6-fluoro-1,4-dihydro-7-[3-(R)-hydroxy-1-pyrrolidinyl]-4-oxo-3-quinolinecarboxylic acid,
sodium 1-cyclopropyl-6-fluoro-1,4-dihydro-7-[3-(S)-hydroxy-1-pyrrolidinyl]-4-oxo-3-quinolinecarboxylate,
potassium 1-cyclopropyl-6-fluoro-1,4-dihydro-7-[3-(R)-hydroxy-1-pyrrolidinyl]-4-oxo-3-quinolinecarboxylate,
sodium 8-chloro-1-cyclopropyl-6-fluoro-1,4-dihydro-7-[3-(S)-hydroxy-1-pyrrolidinyl]-4-oxo-3-quinolinecarboxylate,
silver 8-chloro-1-cyclopropyl-6-fluoro-1,4-dihydro-7-[3-(R)-hydroxy-1-pyrrolidinyl]-4-oxo-3-quinolinecarboxylate,
methyl 1-cyclopropyl-6-fluoro-1,4-dihydro-7-[3-(S)-hydroxy-1-pyrrolidinyl]-4-oxo-3-quinolinecarboxylate,
ethyl 1-cyclopropyl-6-fluoro-1,4-dihydro-7-[3-(R)-hydroxy-1-pyrrolidinyl]-4-oxo-3-quinolinecarboxylate,
ethyl 8-chloro-1-cyclopropyl-6-fluoro-1,4-dihydro-7-[3-(S)-hydroxy-1-pyrrolidinyl]-4-oxo-3-quinolinecarboxylate,
propyl 8-chloro-1-cyclopropyl-6-fluoro-1,4-dihydro-7-[3-(R)-hydroxy-1-pyrrolidinyl]-4-oxo-3-quinolinecarboxylate,
5-methyl-2-oxo-1,3-dioxol-4-ylmethyl 1-cyclopropyl-6-fluoro-1,4-dihydro-7-[3-(S)-hydroxy-1-pyrrolidinyl]-4-oxo-3-quinolinecarboxylate,
5-methyl-2-oxo-1,3-dioxol-4-ylmethyl 1-cyclopropyl-6-fluoro-1,4-dihydro-7-[3-(R)-hydroxy-1-pyrrolidinyl]-4-oxo-3-quinolinecarboxylate,
5-methyl-2-oxo-1,3-dioxol-4-ylmethyl 8-chloro-1-cyclopropyl-6-fluoro-1,4-dihydro-7-[3-(S)-hydroxy-1-pyrrolidinyl]-4-oxo-3-quinolinecarboxylate,
5-methyl-2-oxo-1,3-dioxol-4-ylmethyl 8-chloro-1-cyclopropyl-6-fluoro-1,4-dihydro-7-[3-(R)-hydroxy-1-pyrrolidinyl]-4-oxo-3-quinolinecarboxylate,
1-cyclopropyl-6-fluoro-1,4-dihydro-7-[3-(S)-hydroxymethyl-1-pyrrolidinyl]-4-oxo-3-quinolinecarboxylic acid,
1-cyclopropyl-6-fluoro-1,4-dihydro-7-[3-(R)-hydroxymethyl-1-pyrrolidinyl]-4-oxo-3-quinolinecarboxylic acid,
8-chloro-1-cyclopropyl-6-fluoro-1,4-dihydro-7-[3-(S)-hydroxymethyl-1-pyrrolidinyl]-4-oxo-3-quinolinecarboxylic acid,
8-chloro-1-cyclopropyl-6-fluoro-1,4-dihydro-7-[3-(R)-hydroxymethyl-1-pyrrolidinyl]-4-oxo-3-quinolinecarboxylic acid,
ethyl 1-cyclopropyl-6,8-difluoro-1,4-dihydro-7-(3-hydroxymethyl-1-pyrrolidinyl)-4-oxo-3-quinolinecarboxylate,
1-cyclopropyl-6-fluoro-1,4-dihydro-7-(3-hydroxymethyl-1-pyrrolidinyl)-4-oxo-1,8-naphthyridine-3-carboxylic acid,
1-cyclopropyl-6,8-difluoro-1,4-dihydro-7-[3-(S)-mercapto-1-pyrrolidinyl]-4-oxo-3-quinolinecarboxylic acid,
1-cyclopropyl-6-fluoro-1,4-dihydro-7-[3-(R)-mercapto-1-pyrrolidinyl]-4-oxo-3-quinolinecarboxylic acid,
8-chloro-1-cyclopropyl-6-fluoro-1,4-dihydro-7-[3-(S)-mercapto-1-pyrrolidinyl]-4-oxo-3-quinolinecarboxylic acid,
8-chloro-1-cyclopropyl-6-fluoro-1,4-dihydro-7-[3-(R)-mercapto-1-pyrrolidinyl]-4-oxo-3-quinolinecarboxylic acid,
1-cyclopropyl-6-fluoro-1,4-dihydro-7-(3-mercapto-1-pyrrolidinyl)-4-oxo-1,8-naphthyridine-3-carboxylic acid.

EXAMPLE OF A TABLET ACCORDING TO THE INVENTION

Each tablet contains:

| | |
|---|---|
| Compound of Example 1 | 583.0 mg |
| Microcrystalline cellulose | 55.0 mg |
| Corn starch | 72.0 mg |

| -continued | |
|---|---|
| Poly-(1-vinyl-2-pyrrolidone) insoluble | 30.0 mg |
| Highly disperse silicon dioxide | 5.0 mg |
| Magnesium stearate | 5.0 mg |
| | 750.0 mg |

The lacquer coating contains:

| Poly-(0-hydroxypropyl-0-methyl)-cellulose 15 cp | 6.0 mg |
|---|---|
| Macrogol 4000 rec. INN polyethylene glycols (DAB) | 2.0 mg |
| Titanium(IV) oxide | 2.0 mg |
| | 10.0 mg |

The compounds according to the invention exhibit low toxicity and a broad antibacterial spectrum against Gram-positive and Gram-negative organisms, in particular against enterobacteriaceae; especially including those resistant to various antibiotics such as, for example, penicillins, cephalosporins, aminoglycosides, sulphonamides and tetracyclines.

These valuable properties permit their use as chemotherapeutic active compounds in medicine and as compounds for preserving inorganic and organic materials, in particular organic materials of all kinds, for example polymers, lubricants, paints, fibers, leather, paper and timber, foodstuffs and water.

The compounds according to the invention are active against a very broad spectrum of microorganisms. They can be used to combat Gram-negative and Gram-positive bacteria and bacteria-like microorganisms and to prevent, ameliorate and/or heal illnesses caused by these pathogens.

The compounds according to the invention are particularly active against bacteria and bacteria-like microorganisms. They are therefore particularly suitable for the prophylaxis and chemotherapy of local and systemic infections, caused by these pathogens, in human medicine and veterinary medicine.

For example, local and/or systemic illnesses caused by the following pathogens or by mixtures of the following pathogens can be treated and/or prevented:

Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoeae*) and Gram-negative rods such as Enterobacteriaceae, for example *Escherichia coli, Haemophilus influenzae,* Citrobacter (*Citrob. freundii, Citrob. divernis*), Salmonella and Shigella; also Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the genus Acinetobacter. The antibacterial spectrum also embraces the genus Pseudomonas (*Ps. aeruginosa* and *Ps. maltophilia*) and strict anaerobic bacteria such as, for example, *Bacteroides fragilis,* representatives of the genus Peptococcus, Peptostreptococcus and the genus Clostridium; furthermore Mycoplasmae (*M. pneumoniae, M. hominis* and *M. urealyticum*) and Mucobacteria, for example *Mycobacterium tuberculosis.*

The above list of pathogens is purely illustrative and is in no way to be interpreted as restrictive. The following may be mentioned as examples of illnesses which are caused by the said pathogens or mixed infections and which can be prevented, ameliorated and/or healed by the compounds according to the invention:

Infectious illnesses in humans such as, for example, otitis, pharyngitis, pneumonia, peritonitis, pyelonephritis, cystitis, endocarditis, systemic infections, bronchitis (acute or chronic), septic infections, illnesses of the upper respiratory tract, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, post-operative wound infections, abscesses, phlegmon, wound infections, infected burns, burns, infections of the mouth, infections following dental surgery, osteomyelitis, septic arthritis, cholecystitis, peritonitis with appendicitis, cholangitis, intraabdominal abscesses, pancreatitis, sinusitis, mastoiditis, mastitis, tonsillitis, typhoid, meningitis and infections of the nervous system, salpingitis, endometritis, genital infections, pelveoperitonitis and eye infections.

Apart from humans, bacterial infections in other species can also be treated. Examples which may be mentioned are:

pigs: coli diarrhoea, enterotoxaemia, sepsis, dysentery, salmonellosis, mastitis-metritis-agalactia syndrome and mastitis;

ruminants (cattle, sheep and goats): diarrhoea, sepsis, bronchopneumonia, salmonellosis, pasteurellosis, mycoplasmosis and genital infections;

horse: bronchopneumonia, joint ill, puerperal and post-puerperal infections and salmonellosis;

dog and cat: bronchopneumonia, diarrhoea, dermatitis, otitis, urinary tract infections and prostatitis;

poultry (chicken, turkey, quail, pigeon, ornamental birds and others): mycoplasmosis, *E. coli* infections, chronic respiratory tract illnesses, salmonellosis, pasteurellosis and psittacosis.

It is equally possible to treat bacterial illnesses during rearing and maintenance of useful and ornamental fish, in which case the antibacterial spectrum is extended beyond the abovementioned pathogens to further pathogens such as, for example, Pasteurella, Brucella, Campylobacter, Listeria, Erysipelothrix, Corynebacteria, Borrelia, Treponema, Nocardia, Rikettsia and Yersinia.

The present invention includes pharmaceutical preparations which, in addition to non-toxic, inert pharmaceutically suitable excipients, contain one or more compounds according to the invention or which consist of one or more active compounds according to the invention, as well as processes for the manufacture of these preparations.

The present invention also includes pharmaceutical preparation in dosage units. This means that the preparation is in the form of individual parts, for example tablets, coated tablets, capsules, pills, suppositories and ampules, of which the content of active compound correspond to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerine, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound or compounds, for example lactose, talc, silica, aluminum hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such as solvents, solubilizing agents, and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerine, glycerineformal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary excipients in addition to the active compound or compounds, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminum meta-hydroxide, bentonite, agar-agar and tragacanth or mixtures of these substances.

The formulation forms mentioned can also contain dyestuffs, preservatives and additives which improve the odor and flavor, for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, percent by weight of the total mixture.

The abovementioned pharmaceutical preparations can also contain other pharmaceutical active compounds in addition to the compounds according to the invention.

The abovementioned pharmaceutical preparations are manufactured in the usual manner according to known methods, for example by mixing the active compound or the active compounds with the excipient or excipients.

The said preparations can be used in humans and animals either orally, rectally, parenterally (intravenously, intramuscularly or subcutaneously), intracisternally, intravaginally, intraperitoneally, topically (powder, ointment and drops) and for the therapy of infections in hollow spaces and body cavities. Suitable preparations are injection solutions, solutions and suspensions for oral therapy, gels, pour-on formulations, emulsions, ointments or drops. It is possible to use for topical therapy ophthalmological and dermatological formulations, silver and other salts, ear drops, eye ointments, powders or solutions. In animals, intake can also be effected via the feed or drinking water in suitable formulations. It is also possible to use gels, oral powders, powders, tablets, retard tablets, premixes, concentrates, granules, pellets, boli, capsules, aerosols, sprays and inhalates in humans and animals. It is also possible to incorporate the compounds according to the invention in other excipients such as, for example, plastics (plastic chains for local therapy), collagen or bone cement.

In general it has proved advantageous both in human medicine and in veterinary medicine to administer the active compound or compounds according to the invention in total amounts of about 0.5 to about 500, preferably 5 to 100, mg/kg of body weight every 24 hours, optionally in the form of several individual administrations, in order to achieve the desired results. An individual administration contains the active compound or active compounds according to the invention preferably in amounts of about 1 to about 80, especially of 3 to 30, mg/kg of body weight. However, it can be necessary to deviate from the dosages mentioned and in particular to do so as a function of the nature and body weight of the subject to be treated, the nature and the severity of the illness, the nature of the preparation and of the administration of the medicine, and the time or interval over which the administration takes place.

Thus it can suffice in some cases to manage with less than the abovementioned amount of active compound while in other cases the abovementioned amount of active compound must be exceeded. The particular required optimum dosage and the type of administration of the active compounds can easily be decided by anyone skilled in the art, on the basis of his expert knowledge.

The new compounds can be administered, in the usual concentrations and preparations, together with the feedstuff or the feedstuff preparations, or with the drinking water. It is possible in this way to prevent, ameliorate and/or cure an infection by Gram-negative or Gram-positive bacteria, and hence to achieve an acceleration of growth and an improvement in feedstuff utilization.

The table which follows specifies MIC values for some of the compounds according to the invention, compared with ciprofloxacin.

| Organisms | MIC values (mg/l)* Example 1 | Example 3 | Ciprofloxacin |
|---|---|---|---|
| *E. coli* | | | |
| 4418 | <0.015 | ≦0.015 | ≦0.015 |
| Neumann | ≦0.015 | ≦0.015 | ≦0.015 |
| T7 | <0.015 | ≦0.015 | ≦0.015 |
| 455/7 | 32 | 0.25 | 1 |
| A261 | <0.015 | ≦0.015 | ≦0.015 |
| *Klebsiella pneum.* | | | |
| 63 | <0.015 | ≦0.015 | 0.03 |
| 8085 | ≦0.015 | ≦0.015 | ≦0.015 |
| 6179 | 0.125 | <0.015 | 0.125 |
| 57USA | 0.125 | ≦0.015 | ≦0.015 |
| 6318 | 0.06 | ≦0.015 | 0.06 |
| *Proteus mir.* | | | |
| 8223 | 2 | 0.06 | 4 |
| 8175 | 0.06 | ≦0.015 | 0.06 |
| *Proteus vulg.* | | | |
| 1017 | ≦0.015 | ≦0.015 | ≦0.015 |
| *Proteus morg.* | | | |
| 932 | ≦0.015 | ≦0.015 | <0.015 |
| 11006 | ≦0.015 | ≦0.015 | ≦0.015 |
| *Providencia stuartei* | | | |
| 12012 | ≦0.015 | ≦0.015 | ≦0.015 |
| 12052 | 32 | 1 | 16 |
| *Serratia marc.* | | | |
| 16040 | 32 | 1 | 8 |
| *Staph. aureus* | | | |
| FK422 | ≦0.015 | ≦0.015 | 0.5 |
| 1756 | ≦0.015 | ≦0.015 | 0.25 |
| 133 | ≦0.015 | ≦0.015 | 0.25 |
| *Strepto. faecalis* | | | |
| 27101 | 0.125 | ≦0.015 | 0.25 |
| 9790 | 0.125 | ≦0.015 | 0.5 |
| *Psdm. aeruginosa* | | | |
| Walter | 1 | 0.25 | 0.5 |
| Ellsworth | 0.125 | ≦0.015 | 0.06 |

*Agar dilution test (multipoint inoculator) Isosensitest medium pH 7.2

EXAMPLE 1

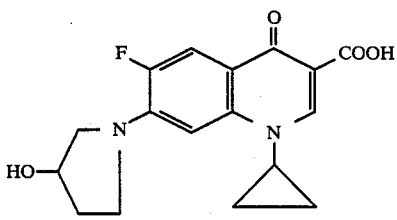

To 7.95 g (30 mmol) of 1-cyclopropyl-6,7-difluoro-1,4-dihydro-4-oxo-3-quinolinecarboxylic acid in a mixture of 60 ml of acetonitrile and 30 ml of dimethylformamide are added 3.9 g (31 mmol) of 3-hydroxypyrrolidine hydrochloride (racemate) and 9.9 g (88 mmol) of 1,4-diazabicyclo[2.2.2]octane, and the mixture is refluxed for 3 hours. The suspension is concentrated, the residue is stirred up with about 100 ml of water, and the mixture is brought to pH 6-7 with 2N hydrochloric acid. The undissolved reaction product is filtered off with suction, washed with water and dried.

Yield: 9.3 g (93.3% of theory) of 1-cyclopropyl-6-fluoro-1,4-dihydro-7-(3-hydroxy-1-pyrrolidinyl)-4-oxo-3-quinolinecarboxylic acid having a melting point of 325° C.–328° C. (with decomposition).

EXAMPLE 2

2.65 g (10 mmol) of 1-cyclopropyl-6,7-difluoro-1,4-dihydro-4-oxo-3-quinolinecarboxylic acid are heated at 130° C. for 3 hours in 6 ml of dimethyl sulphoxide together with 1 g (11 mmol) of 3-hydroxypyrrolidine (racemate) and 2.2 g (20 mmol) of 1,4-diazabicyclo[2.2.2]octane. After cooling down, the suspension is stirred up with 30 ml of water and brought to pH 6-7 with 2N hydrochloric acid, and the precipitate is filtered off with suction, washed with water and boiled up in 30 ml of glycol monomethyl ether. This gives 2.7 g (81% of theory) of 1-cyclopropyl-6-fluoro-1,4-dihydro-7-(3-hydroxy-1-pyrrolidinyl)-4-oxo-3-quinolinecarboxylic acid having a melting point of 332°–336° C. (with decomposition). According to thin layer chromatography the compound is identical to the compound of Example 1.

EXAMPLE 3

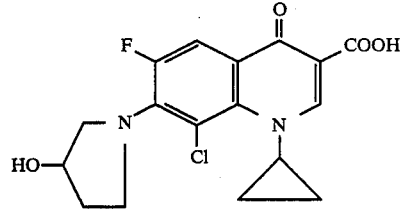

To 1.5 g (5 mmol) of 8-chloro-1-cyclopropyl-6,7-difluoro-1,4-dihydro-4-oxo-3-quinolinecarboxylic acid in 10 ml of acetonitrile and 5 ml of dimethylformamide are added 1.1 g (10 mmol) of 1,4-diazabicyclo[2.2.2]octane and 650 mg (5.3 mmol) of 3-hydroxypyrrolidine hydrochloride and the mixture is refluxed for 3 hours. The suspension is concentrated, the residue is stirred up with water and brought to pH 6-7 with 2N hydrochloric acid, and the precipitate is filtered off with suction, dried and recrystallized from glycol monomethyl ether.

Yield: 1.2 g (65% of theory) of 8-chloro-1-cyclopropyl-7-fluoro-1,4-dihydro-7-(3-hydroxy-1-pyrrolidinyl)-4-oxo-3-quinolinecarboxylic acid having a melting point of 221°–223° C. (with decomposition).

EXAMPLE 4

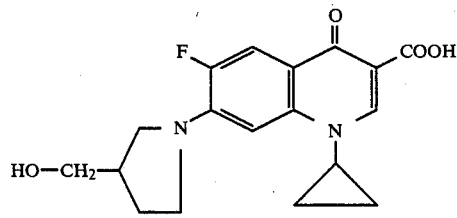

Example 1 is repeated with 3-hydroxymethylpyrrolidine, affording 1-cyclopropyl-6-fluoro-1,4-dihydro-7-(3-hydroxymethyl-1-pyrrolidinyl)-3-quinolinecarboxylic acid having a melting point of 278°–281° C. (with decomposition).

The same method is used to obtain:

8-chloro-1-cyclopropyl-6-fluoro-1,4-dihydro-7-(3-hydroxymethyl-1-pyrrolidinyl)-3-quinolinecarboxylic acid having a melting point of 160°–162° (with decomposition);

1-cyclopropyl-6,8-difluoro-1,4-dihydro-7-(3-hydroxymethyl-1-pyrrolidinyl)-3-quinolinecarboxylic acid having a melting point of 236°–240° C. (with decomposition).

It will be understood that the specification and examples are illustrative but not limitative of the present invention and that other embodiments within the spirit and scope of the invention will suggest themselves to those skilled in the art.

What is claimed is:

1. A 7-(1-pyrrolidinyl)-3-quinolonecarboxylic acid derivative having the formula

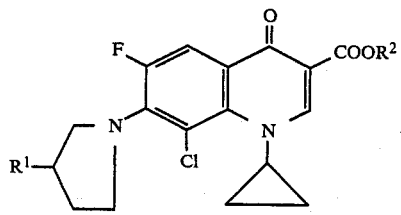

in which $R^1$ is hydroxymethyl and $R^2$ is hydrogen, or alkyl, having 1 to 4 carbon atoms, or a pharmaceutically acceptable hydrate, alkali metal alkaline earth metal, silver or guanidinium salt.

2. A compound, hydrate or salt according to claim 1, in which $R^2$ is hydrogen, methyl, ethyl, propyl or isopropyl.

3. A compound, hydrate or salt according to claim 1, in which $R^2$ is hydrogen, methyl or ethyl.

4. A compound according to claim 1, wherein such compound is 8-chloro-1-cyclopropyl-6-fluoro-1,4-dihydro-7-(3-hydroxymethyl-1-pyrrolidinyl)-4-oxo-3-quinolinecarboxylic acid of the formula

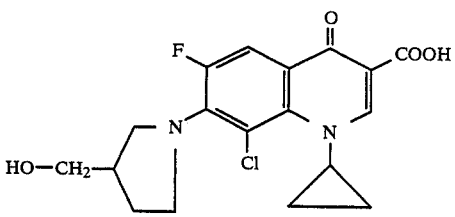

or a pharmaceutically acceptable hydrate, alkali metal, alkaline earth metal, silver or guanidinium salt thereof.

5. An antibacterial composition comprising an antibacterially effective amount of a compound, hydrate or salt according to claim 1 and a pharmaceutically acceptable diluent.

6. A method of combating bacteria which comprises administering to a patient an antibacterially effective amount of a compound, hydrate or salt according to claim 1.

7. The method according to claim 6, wherein such compound is 8-chloro-1-cyclopropyl-6-fluoro-1,4-dihydro-7-(3-hydroxymethyl-1-pyrrolidinyl)-4-oxo-3-quinolinecarboxylic acid, or a pharmaceutically acceptable hydrate, alkali metal, alkaline earth metal, silver or guanidinium salt thereof.

8. An animal growth promoting composition comprising an animal growth promoting effective amount of a compound, hydrate or salt according to claim 1 and edible feed base.

9. A method of promoting the growth of animals which comprises feeding said animals an animal growth promoting effective amount of a compound, hydrate or salt according to claim 1.

10. The method according to claim 9, wherein such compound is 8-chloro-1-cyclopropyl-6-fluoro-1,4-dihydro-7-(3-hydroxymethyl-1-pyrrolidinyl)-4-oxo-3-quinolinecarboxylic acid, or a pharmaceutically acceptable hydrate, alkali metal, alkaline earth metal, silver or guanidinium salt thereof.

* * * * *